US008840884B2

(12) United States Patent
Kakuta et al.

(10) Patent No.: US 8,840,884 B2
(45) Date of Patent: Sep. 23, 2014

(54) ANTIBODY-CONTAINING SOLUTION PHARMACEUTICALS

(75) Inventors: Masaya Kakuta, Shizuoka (JP); Jun Kikuchi, Tokyo (JP); Hidefumi Mizushima, Tokyo (JP); Yoshimi Imaeda, Tokyo (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 10/503,720

(22) PCT Filed: Feb. 14, 2003

(86) PCT No.: PCT/JP03/01563
§ 371 (c)(1),
(2), (4) Date: Apr. 27, 2005

(87) PCT Pub. No.: WO03/068260
PCT Pub. Date: Aug. 21, 2003

(65) Prior Publication Data
US 2005/0214278 A1 Sep. 29, 2005

(30) Foreign Application Priority Data

Feb. 14, 2002 (JP) .................................. 2002-36244

(51) Int. Cl.
*C07K 16/44* (2006.01)
*A61K 39/395* (2006.01)
*A61K 47/26* (2006.01)
*C07K 16/30* (2006.01)
*A61K 9/00* (2006.01)
*A61K 47/10* (2006.01)
*A61K 47/12* (2006.01)
*C07K 16/40* (2006.01)
*A61K 39/40* (2006.01)
*A61K 39/00* (2006.01)

(52) U.S. Cl.
CPC ........... *C07K 16/44* (2013.01); *A61K 39/39591* (2013.01); *A61K 47/26* (2013.01); *C07K 16/3061* (2013.01); *A61K 2039/505* (2013.01); *A61K 9/0019* (2013.01); *A61K 47/10* (2013.01); *A61K 47/12* (2013.01); *C07K 16/40* (2013.01)
USPC ................... 424/130.1; 424/133.1; 424/141.1

(58) Field of Classification Search
USPC ...................................................... 424/130.1
See application file for complete search history.

(56) References Cited

U.S. PATENT DOCUMENTS

| | | | |
|---|---|---|---|
| 4,186,192 A | 1/1980 | Lundblad et al. | |
| 5,171,840 A | 12/1992 | Kishimoto | |
| 5,480,796 A | 1/1996 | Kishimoto | |
| 5,635,176 A | 6/1997 | Samaritani et al. | |
| 5,654,403 A | 8/1997 | Smith et al. | |
| 5,656,730 A * | 8/1997 | Lee ............................. | 530/387.3 |
| 5,670,373 A | 9/1997 | Kishimoto | |
| 5,777,085 A | 7/1998 | Co et al. | |
| 5,795,965 A | 8/1998 | Tsuchiya et al. | |
| 5,817,790 A | 10/1998 | Tsuchiya et al. | |
| 5,851,793 A | 12/1998 | Kishimoto | |
| 5,888,510 A | 3/1999 | Kishimoto et al. | |
| 5,945,098 A | 8/1999 | Sarno et al. | |
| 5,990,282 A | 11/1999 | Kishimoto | |
| 6,086,874 A | 7/2000 | Yoshida et al. | |
| 6,165,467 A | 12/2000 | Hagiwara et al. | |
| 6,171,586 B1 * | 1/2001 | Lam et al. .................. | 424/130.1 |
| 6,252,055 B1 | 6/2001 | Relton | |
| 6,261,560 B1 | 7/2001 | Tsujinaka et al. | |
| 6,267,958 B1 | 7/2001 | Andya et al. | |
| 6,406,909 B1 | 6/2002 | Shibuya et al. | |
| 6,410,691 B1 | 6/2002 | Kishimoto | |
| 6,428,979 B1 | 8/2002 | Kishimoto | |
| 6,537,782 B1 | 3/2003 | Shibuya et al. | |
| 6,692,742 B1 | 2/2004 | Nakamura et al. | |
| 6,699,974 B2 * | 3/2004 | Ono et al. ................ | 530/388.85 |
| 6,723,319 B1 | 4/2004 | Ito et al. | |
| 6,962,812 B2 | 11/2005 | Shibuya et al. | |
| 7,320,792 B2 | 1/2008 | Ito et al. | |
| 7,332,289 B2 | 2/2008 | Takeda et al. | |
| 7,479,543 B2 | 1/2009 | Tsuchiya et al. | |
| 7,498,031 B2 | 3/2009 | Fujioka et al. | |
| 7,521,052 B2 | 4/2009 | Okuda et al. | |
| 7,566,453 B2 | 7/2009 | Nakamura et al. | |
| 7,771,723 B2 | 8/2010 | Nakamura et al. | |
| 7,824,674 B2 | 11/2010 | Ito et al. | |
| 7,927,815 B2 | 4/2011 | Takeda et al. | |
| 7,955,598 B2 | 6/2011 | Yoshizaki et al. | |
| 8,017,121 B2 | 9/2011 | Kishimoto et al. | |

(Continued)

FOREIGN PATENT DOCUMENTS

AU 2001277781 2/2002
CA 2201781 4/1996

(Continued)

OTHER PUBLICATIONS

Cleland, Jeffrey L. et al., "A Specific Molar Ratio of Stabilizer to Protein is Required for Storage Stability of a Lyophilized Monoclonal Antibody", Journal of Pharmaceutical Sciences, vol. 90, No. 3, pp. 310-321, Mar. 2001, XP001179875.
Jones et al., L. S., "The Effects of Tween 20 and Sucrose on the Stability of Anti-L-Selectin during Lyophilization and Reconstitution", Journal of Pharmaceutical Sciences, vol. 90, No. 10, pp. 1466-1477 (2001).
Shimizu et al., M., "Egg Yolk Antibody (IgY) Stability in Aqueous Solution with High Sugar Concentrations", Journal of Food Science, vol. 59, No. 4, pp. 763-765, 772 (1994).
Carpenter et al., J. F., "Rational Design of Stable Lyophilized Protein Formulations: Some Practical Advice", Pharmaceutical Research, vol. 14, No. 8, pp. 969-975 (1997).
Wang, Wei, "Instability, Stabilization, and Formulation of Liquid Protein Pharmaceuticals", International Journal of Pharmaceutics, vol. 185, pp. 129-188 (1999).

(Continued)

*Primary Examiner* — Yunsoo Kim
(74) *Attorney, Agent, or Firm* — Browdy and Neimark, PLLC

(57) ABSTRACT

Antibody-containing solution formulations including a sugar as a stabilizer. Said solution formulations can further include a surfactant as a stabilizer.

21 Claims, No Drawings

(56) References Cited

U.S. PATENT DOCUMENTS

| | | |
|---|---|---|
| 2001/0014326 A1 | 8/2001 | Andya et al. |
| 2002/0037288 A1 | 3/2002 | Koishihara et al. |
| 2003/0190316 A1 | 10/2003 | Kakuta et al. |
| 2004/0115197 A1 | 6/2004 | Yoshizaki et al. |
| 2005/0118163 A1 | 6/2005 | Mizushima et al. |
| 2005/0214278 A1 | 9/2005 | Kakuta et al. |
| 2005/0238644 A1 | 10/2005 | Mihara et al. |
| 2006/0134113 A1 | 6/2006 | Mihara |
| 2006/0142549 A1 | 6/2006 | Takeda et al. |
| 2006/0165696 A1 | 7/2006 | Okano et al. |
| 2006/0292147 A1 | 12/2006 | Yoshizaki et al. |
| 2007/0036785 A1 | 2/2007 | Kishimoto et al. |
| 2007/0098714 A1 | 5/2007 | Nishimoto et al. |
| 2007/0134242 A1 | 6/2007 | Nishimoto et al. |
| 2008/0124325 A1 | 5/2008 | Ito et al. |
| 2008/0124761 A1 | 5/2008 | Goto et al. |
| 2008/0188401 A1 | 8/2008 | Cruwys et al. |
| 2008/0274106 A1 | 11/2008 | Nishimoto et al. |
| 2008/0306247 A1 | 12/2008 | Mizushima et al. |
| 2009/0022719 A1 | 1/2009 | Mihara et al. |
| 2009/0131639 A1 | 5/2009 | Kakuta et al. |
| 2009/0181029 A1 | 7/2009 | Okuda et al. |
| 2009/0220499 A1 | 9/2009 | Yasunami |
| 2009/0220500 A1 | 9/2009 | Kobara |
| 2009/0263384 A1 | 10/2009 | Okada et al. |
| 2009/0269335 A1 | 10/2009 | Nakashima et al. |
| 2009/0291076 A1 | 11/2009 | Morichika et al. |
| 2010/0008907 A1 | 1/2010 | Nishimoto et al. |
| 2010/0034811 A1 | 2/2010 | Ishida |
| 2010/0061986 A1 | 3/2010 | Takahaski et al. |
| 2010/0129355 A1 | 5/2010 | Ohguro et al. |
| 2010/0247523 A1 | 9/2010 | Kano et al. |
| 2010/0255007 A1 | 10/2010 | Mihara et al. |
| 2010/0285011 A1 | 11/2010 | Morichika et al. |
| 2010/0304400 A1 | 12/2010 | Stubenrauch et al. |
| 2011/0117087 A1 | 5/2011 | Franze et al. |
| 2011/0150869 A1 | 6/2011 | Mitsunaga et al. |
| 2011/0206664 A1 | 8/2011 | Yoshizaki et al. |
| 2011/0245473 A1 | 10/2011 | Igawa et al. |
| 2011/0262462 A1 | 10/2011 | Platt et al. |
| 2011/0268734 A1 | 11/2011 | Ito et al. |
| 2012/0009177 A1 | 1/2012 | Platt et al. |
| 2012/0183539 A1 | 7/2012 | Maeda |
| 2012/0301460 A1 | 11/2012 | Bao et al. |

FOREIGN PATENT DOCUMENTS

| | | |
|---|---|---|
| CA | 2226575 | 2/1997 |
| CA | 2267072 | 4/1998 |
| CH | 684164 | 7/1994 |
| EP | 0 012 156 A1 | 6/1980 |
| EP | 0 073 371 A2 | 3/1983 |
| EP | 0 122 558 A2 | 10/1984 |
| EP | 0196761 | 10/1986 |
| EP | 0 278 422 A2 | 8/1988 |
| EP | 0479597 | 4/1992 |
| EP | 0 597 101 A1 | 5/1994 |
| EP | 0 628 639 A1 | 12/1994 |
| EP | 0865793 A1 | 9/1998 |
| EP | 0 911 037 A1 | 4/1999 |
| EP | 0 960 936 A1 | 12/1999 |
| EP | 0960936 A1 | 12/1999 |
| EP | 0997152 | 5/2000 |
| EP | 1 174 148 A1 | 1/2002 |
| JP | 60149972 A | 7/1985 |
| JP | 60146832 | 8/1985 |
| JP | 60149972 | 8/1985 |
| JP | 63-088197 A | 4/1988 |
| JP | 3630453 | 3/1995 |
| JP | 08-099902 A | 4/1996 |
| JP | 09-500894 A | 1/1997 |
| JP | 3822137 | 11/2003 |
| JP | 2009092508 | 4/2009 |
| WO | 92/19759 | 11/1992 |
| WO | WO 95/03826 A1 | 2/1995 |
| WO | 97/04801 | 2/1997 |
| WO | 97/45140 A1 | 12/1997 |
| WO | 98/22136 A2 | 5/1998 |
| WO | 98/35698 A1 | 8/1998 |
| WO | WO9842376 A1 | 10/1998 |
| WO | 98/56418 A1 | 12/1998 |
| WO | 0010607 | 3/2000 |
| WO | 00/50639 | 8/2000 |
| WO | 00/66160 | 11/2000 |
| WO | 02/13860 A1 | 2/2002 |
| WO | 0213859 | 2/2002 |
| WO | 03068259 | 8/2003 |
| WO | 03068260 | 8/2003 |
| WO | 2007074880 | 7/2007 |
| WO | 2008016134 | 2/2008 |
| WO | 2008078715 | 7/2008 |
| WO | 2009084659 | 7/2009 |
| WO | 2011149046 | 12/2011 |
| WO | 2011149051 | 12/2011 |
| WO | 2012064627 | 5/2012 |

OTHER PUBLICATIONS

Shinkura et al., "Safety and kinetic properties of a humanized antibody to human interleukin-6 receptor in healthy non-human primates", Toxicology, vol. 122, pp. 163-170 (1997).

Imazeki et al., M., "IL-6 functions in cynomolgus monkeys blocked by a humanized antibody to human IL-6 receptor", International Journal of Immunopharmacology, vol. 20. pp. 345-357 (1998).

Sato et al., "Reshaping a human antibody to inhibit the interleukin 6-dependent tumor cell growth", Cancer Research, vol. 53, pp. 851-856 (1993).

Tsunenari et al., "Therapeutic Potential of Humanized Anti-interleukin-6 Receptor Antibody: Antitumor Activity in Xenograft Model of Multiple Myeloma," Anticancer Research, vol. 16, pp. 2537-2544 (1996).

Hirata et al., "Characterization of IL-6 Receptor Expression by Monoclonal and Polyclonal Antibodies", The Journal of Immunology, vol. 143, No. 9, pp. 2900-2906 (1989).

Suzuki et al., "Anti-human interleukin-6 receptor antibody inhibits human myeloma growth in vivo", Eur. J. Immunol., vol. 22, pp. 1989-1993 (1992).

"Remicade-Infliximab for IV Injection", Retrieved from the Internet: http://www.accessdata.fda.gov/drugsatfda_docs/label/1998/inflcen082498lb.pdf, pp. 1-12, Aug. 12, 1998, XP002616537.

"Herceptin-Trastuzmab (FDA approval)", Retrieved from the Internet: URL: http://www.fda.gov/downloads/Drugs/DevleopementApprovalProcess/HowDrugsareDevelopedandApproved/ApprovalApplications/TherapeuticBiologicApplications/ucm091361.pdf, p. 1, Sep. 1, 1998, XP002616538.

Michael J. Akers et al., "Formulation Development of Protein Dosage Forms", Pharmaceutical Biotechnology, Kluwer, Dordrecht, NL, vol. 14, Jan. 1, 2002, pp. 47-127, XP001537612, ISSN: 1078-0467.

Jeffrey L. Cleland et al., "The Development of Stables Protein Formulations: A Close Look At Protein Aggregation, Deamidation and Oxidation", Critical Review in Therapeutic Drug Carrier Systems, vol. 10, No. 4, pp. 307-377, Jan. 1, 1993, XP002083452, ISSN: 0743-4863.

J. C. Lee et al., "The Stabilization of Proteins by Sucrose", The Journal of Biochemical Chemistry, vol. 256, No. 14, pp. 7193-7201, Jul. 25, 1981, XP002616540, LKND-PUBMED: 7251592, ISSN:0021-9258.

Partial European Search Report of EP 10 01 0404 dated Jan. 28, 2011.

CAS entry for registration No. 375823-41-9, Immunoglobulin G2, anti-(human interleukin 6 receptor) (human-mouse monoclonal MRA heavy chain), disulfide with human-mouse monoclonal MRA fE-chain, dimer, 4 pp., Dec. 17, 2001.

European Medicines Agency, Evaluation of Medicines of Human Use, pp. 1-55, 2009.

Gejima, et al., Human single-chain Fv (scFv) antibody specific to human IL-6 with the inhibitory activity on IL-6-signaling, Human Antibodies, vol. 11, pp. 121-129, 2002.

Nishimoto, et al., Anti-interleukin 6 receptor antibody treatment in rheumatic disease, Ann. Rheum Dis, vol. 59 (suppl 1), pp. i21-i27, 2000.

(56) References Cited

OTHER PUBLICATIONS

Supplementary European Search Report from EP Application No. 03 70 5166; dated Mar. 24, 2005.
EPO Communication from European Application No. 03 705 166.1-2402, dated Jul. 1, 2005.
Vossius & Partner Response filed in European Application No. 03 705 166.1-2402, dated Nov. 11, 2005.
EPO Communication from European Application No. 03 705 166.1-2402, dated Dec. 20, 2005.
Vossius & Partner Response filed in European Application No. 03 705 166.1-2402, dated Apr. 28, 2006.
EPO Communication from European Application No. 03 705 166.1-2402, dated Aug. 22, 2007.
Vossius & Partner Response filed in European Application No. 03 705 166.1-2402, dated Jan. 2, 2008.
EPO Summons to attend oral proceedings from European Application No. 03 705 166.1-2402, dated Jul. 28, 2008.
Vossius & Partner Preparation of Oral Proceedings filed in European Application No. 03 705 166.1-2402, dated Dec. 23, 2008.
Vossius & Partner Auxiliary Request filed in European Application No. 03 705 166.1-2402, dated Jan. 16, 2009.
EPO Communication from European Application No. 03 705 166.1-2402, dated Feb. 4, 2009.
Vossius & Partner Response filed in European Application No. 03 705 166.1-2402, dated Aug. 13, 2009.
EPO Minutes of Oral Proceedings from European Application No. 03 705 166.1-2402, dated Sep. 17, 2009.
Vossius & Partner Response filed in European Application No. 03 705 166.1-2402, dated Feb. 4, 2010.
EPO Result of Consultation from European Application No. 03 705 166.1-2402, dated Feb. 18, 2010.
Vossius & Partner Response filed in European Application No. 03 705 166.1-2402, dated Feb. 19, 2010.
EPO Intent to Grant (signatures), SEction IV.2-4 from European Application No. 03 705 166.1-2402, dated Mar. 25, 2010.
EPO Communication from European Application No. 03 705 166.1-2402, dated Oct. 20, 2009.
Draber, et al., Stability of monoclonal IgM antibodies freeze-dried in the presence of trehalose, Journal of Immunological Methods, 1995, pp. 37-43, vol. 181.
Haskin, et al., Abstract Only, Acute renal failure after large doses of intravenous immune globulin, The Annals of Pharmacotherapy, 1999, pp. 800-803, vol. 33, No. 7-8.
Austrian Patent Office Search Report for Application No. UAE/P/290/2004, Austrian mail date Jun. 20, 2012, UAE mail date Sep. 2, 2012.
Wikipedia, Polysorbate, http://en.wikipedia.org/wiki/Polysorbate, Apr. 22, 2011, pp. 1-2.
Amano, et al., Antigen-Dependent Internalization is Related to Rapid Elimination from Plasma of Humanized Anti-HM1.24 Monoclonal Antibody, Drug Metabolism and Disposition, 2010, pp. 2339-2346, vol. 38, No. 12.
Hirata, et al., Humanized anti-interleukin-6 receptor monoclonal antibody induced apoptosis of fresh and cloned human myeloma cells in vitro, Leukemia Research, 2003, pp. 343-349, vol. 27.
Ozaki, et al., Humanized Anti-HM1.24 Antibody Mediates Myeloma Cell Cytotoxicity That Is Enhanced by Cytokine Stimulation of Effector Cells, Blood, Jun. 1, 1999, pp. 3922-3930, vol. 93, No. 11.

Spierenburg, et al., Phototoxicity of N-2-Hydroxyethylpiperazine-N'-2-ethanesulfonic Acid-buffered Culture Media for Human Leukemic Cell Lines, Cancer Research, May 1984, pp. 2253-2254, vol. 44.
Tsunenari, et al., New Xenograft Model of Multiple Myeloma and Efficacy of a Humanized Antibody Against Human Interleukin-6 Receptor, Blood, Sep. 15, 1997, pp. 2437-2444, vol. 90, No. 6.
Actemra (Tocilizumab), Highlights on Prescribing Information, pp. 1-31 (Oct. 2012).
Kahl, Gunter, The Dictionary of Gene Technology, Genomics, Transcriptomics, Proteomics, Third Edition, 2004, cover page, pp. 49-50 and 387.
Nill, Kimball, Glossary of Biotechnology and Nanobiotechnology Terms, Fourth Edition, 2006, cover page, pp. 22-23.
Hood, et al., Immunology, Second Edition, 1984, cover page, pp. 6-8, 17, 21-24, 31-37.
Genentech, Actemra® (tocilizumab)Injection, for intravenous infusion, Highlights of Prescribing Information and Full Prescribing Information, revised Apr. 2013, pp. 1-36.
Chang, et al., Surface-Induced Denaturation of Proteins during Freezing and its Inhibition by Surfactants, Journal of Pharmaceutical Sciences, Dec. 1996, pp. 1325-1330, vol. 85, No. 12.
Costantino, Excipients for Use in Lyophilized Pharmaceutical Peptide, Protein, and other Bioproducts, in Costantino, Biotechnology: Pharmaceutical Aspects, Lyophilization of Biopharmaceuticals, vol. II, pp. 139, 185, 219, (AAPS Press: 2004).
Duddu, et al., Effect of Glass Transition Temperature on the Stability of Lyophilized Formulations Containing a Chimeric Therapeutic Monoclonal Antibody, Pharmaceutical Research, 1997, pp. 591-595, vol. 14, No. 5.
Duddu, et al., The Relationship Between Protein Aggregation and Molecular Mobility Below the Glass Transition Temperature of Lyophilized Formulations Containing a Monoclonal Antibody, Pharmaceutical Research, 1997, pp. 596-600, vol. 14, No. 5.
European Search Report for EP Application No. 10010404.1-1412, mail date Jul. 18, 2013.
International Conference on Harmonisation of Technical Requirements for Registration of Pharmaceuticals for Human Use (ICH) Working Group, ICH Harmonised Tripartite Guideline, Stability Testing: Photostability Testing of New Drug Substances and Produces Q1B, pp. cover pp. 1-2, table of contents, and pp. 1-8, (Current Step 4 version, Nov. 6, 1996).
Latypov, et al., Elucidation of Acid-induced Unfolding and Aggregation of Human Immunoglobulin IgG1 and IgG2 Fc, The Journal of Biological Chemistry, Jan. 6, 2012, pp. 1381-1396, vol. 287, No. 2.
Nema, et al., Formulation of protein- and peptide-based parenteral products, Pharmaceutical Dosage Forms, Parenteral Medications, vol. 1, title page, pp. 234, 235 and 252, (Informa HealthCare: third edition, 1984).
Pikal, et al., The Effects of Formulation Variables on the Stability of Freeze-Dried Human Growth Hormone, Pharmaceutical Research, 1991, pp. 427-436, vol. 8, No. 4.
Pikal-Cleland, et al., Protein Denaturation during Freezing and Thawing in Phosphate Buffer Systems: Monomeric and Tetrameric. beta-Galactosidase, Archives of Biochemistry and Biophysics, Dec. 15, 2000, pp. 398-406, vol. 384, No. 2.
Sarciaux, et al., Effects of Buffer Composition and Processing Conditions on Aggregation of Bovine IgG during Freeze-Drying, Journal of Pharmaceutical Sciences, Dec. 1999, vol. 88, No. 12.

* cited by examiner

ANTIBODY-CONTAINING SOLUTION PHARMACEUTICALS

TECHNICAL FIELD

The present invention relates to stable antibody-containing solution formulations.

BACKGROUND ART

With the development of genetic engineering technology, it has become possible to use antibodies such as immunoglobulins, monoclonal antibodies and humanized antibodies as pharmaceutical products. To supply them in stable amounts, it is necessary to establish preparation conditions and storage conditions under which the structure and activity of the antibodies can be retained.

When proteins are stored in high concentration solutions, they normally suffer deterioration such as the formation of insoluble aggregates, which must be prevented. Especially, antibody formulations have the disadvantage that they tend to form multimers leading to insoluble aggregates during storage in solutions.

For example, we found that anti-IL-6 receptor antibodies have a therapeutic effect on immature myeloma cells (JPA HEI 8-99902) and succeeded in mass-producing a reshaped humanized antibody, hPM-1 antibody, as an anti-IL-6 receptor antibody, and we have tried to formulate this purified anti-IL-6 receptor antibody into pharmaceutical products. The humanized anti-IL-6 receptor antibody is an unstable protein liable to physical or chemical changes such as association or aggregation under the stresses of filtration, concentration, heat and light for removing viruses and other microbials during purification processes.

When antibodies are to be obtained by genetic engineering techniques, antibody-producing cells are cultured in bulk and purified to give an antibody-containing solution, which is then stored frozen and thawed before formulation. However, the antibody content remaining in such a solution decreased as antibody dimers or insoluble particles were formed during repeated freeze/thaw cycles or antibodies were degraded to form degradation products during long-term storage.

Many efforts have been made to provide a method for storing proteins in solutions, and a stabilization effect was found by adding polymers including proteins such as human serum albumin or purified gelatin or oligomers such as polyols, amino acids and surfactants as stabilizers for preventing chemical or physical changes. However, the addition of biopolymers such as proteins as stabilizers was inconvenient, e.g. it required a very complicated step for eliminating contaminants such as viruses and prions. As to the addition of oligomers, it should preferably be minimized.

Freeze-dried antibody formulations stabilized with sugars or amino sugars, amino acids and surfactants have also been reported (JPA HEI2001-503781).

However, stable antibody-containing solution formulations have been sought because of great demands for easy-to-use solution formulations that may not be dissolved/reconstituted before use.

DISCLOSURE OF THE INVENTION

An object of the present invention is to provide antibody-containing solution formulations in which the antibody content remains high, and which are stable even after long-term storage by inhibiting the formation of insoluble particles and multimers during the preparation or storage of the antibody-containing solution formulations and further inhibiting the formation of degradation products.

As a result of careful studies to attain the above object, we accomplished the present invention on the basis of the finding that the formation of dimers during freeze/thaw cycles or the formation of multimers and degradation products during long-term storage can be inhibited by adding a sugar, and that the formation of insoluble particles during freeze/thaw cycles can be remarkably inhibited by adding a surfactant.

Accordingly, the present invention provides:

(1) an antibody-containing solution formulation including a sugar as a stabilizer;

(2) the solution formulation as defined in (1) further including a surfactant as a stabilizer;

(3) the solution formulation as defined in (1) or (2) wherein the sugar is a sugar alcohol or a nonreducing oligosaccharide;

(4) the solution formulation as defined in (1) or (2) wherein the sugar is a nonreducing oligosaccharide;

(5) the solution formulation as defined in (1) or (2) wherein the sugar is mannitol, sucrose, trehalose or raffinose;

(6) the solution formulation as defined in (1) or (2) wherein the sugar is sucrose, trehalose or raffinose;

(7) the solution formulation as defined in (1) or (2) wherein the sugar is sucrose or trehalose;

(8) the solution formulation as defined in (1) or (2) wherein the sugar is sucrose;

(9) the solution formulation as defined in any one of (2) to (8) wherein the surfactant is Polysorbate 80 or 20;

(10) the solution formulation as defined in any one of (1) to (9) wherein the antibody is a recombinant antibody;

(11) the solution formulation as defined in (10) wherein the antibody is a chimeric antibody, humanized antibody or human antibody;

(12) the solution formulation as defined in any one of (1) to (11) wherein the antibody is an IgG class antibody;

(13) the solution formulation as defined in (12) wherein the IgG class antibody is an IgG1 class antibody;

(14) the solution formulation as defined in any one of (1) to (13) wherein the antibody is an anti-interleukin-6 receptor antibody or anti-HM1.24 antibody;

(15) a method for inhibiting the formation of antibody multimer molecules in an antibody-containing solution formulation, comprising adding a sugar to the solution;

(16) a method for inhibiting the formation of antibody multimer molecules during freeze/thaw cycles of an antibody-containing solution, comprising adding a nonreducing oligosaccharide to the solution;

(17) a method for inhibiting the formation of antibody multimer molecules during freeze/thaw cycles of an antibody-containing solution, comprising adding a nonreducing disaccharide or nonreducing trisaccharide into the solution;

(18) a method for inhibiting the formation of insoluble particles during freeze/thaw cycles of an antibody-containing solution, comprising adding a surfactant; and

(19) a method for stabilizing an antibody during freeze/thaw cycles of a solution containing the antibody, comprising adding a nonreducing sugar and a surfactant.

THE MOST PREFERRED EMBODIMENTS OF THE INVENTION

As used herein, "antibody-containing solution formulation" means a solution formulation containing an antibody as an active ingredient and prepared for administration to animals such as humans, preferably without including any freeze-drying steps in the preparation process.

As used herein, "antibody-containing solution" may be a solution containing any antibody, whether biologically derived or recombinant, preferably a culture medium in which mammalian cells such as CHO cells containing an antibody have been cultured, or a solution obtained by subjecting such a medium to a given treatment such as partial purification (bulk solution), or the solution formulation prepared for administration to animals such as humans as defined above.

As used herein, the term "insoluble particles" means insoluble particulate matters of 10 μm or more as defined in the section of Insoluble Particulate Matter Test for Injections in the part of General Tests, Processes and Apparatus in the Japanese Pharmacopoeia. Insoluble particles can be measured by using microscopes, insoluble particle-collecting filters and analytical membrane filters, or conveniently using automatic light obscuration particle counters.

As used herein, "insoluble matters" mean readily detectable insoluble matters from which injections must be free and clear when inspected in containers with the unaided eye with a light intensity of approximately 1000 luxes under an incandescent lamp as defined in the section of Foreign Insoluble Matter Test for Injections in the part of General Tests, Processes and Apparatus in the Japanese Pharmacopoeia.

As used herein, "multimers" and "degradation products" mean multimers and degradation products respectively of antibody molecules constituting active ingredients of formulations, and their contents can be determined by the peak area percentage method based on gel permeation chromatography described later.

Antibodies used in solution formulations of the present invention are not specifically limited so far as they bind to a desired antigen, and mouse antibodies, rat antibodies, rabbit antibodies, sheep antibodies, chimeric antibodies, humanized antibodies, human antibodies and the like can be used as appropriate. The antibodies may be polyclonal or monoclonal, but preferably monoclonal because homogeneous antibodies can be stably produced. Polyclonal and monoclonal antibodies can be prepared by processes well known to those skilled in the art.

Hybridomas producing monoclonal antibodies can be basically constructed by known techniques as follows. A desired antigen or a cell expressing a desired antigen is used as an immunizing antigen to immunize host cells according to a standard immunization technique, and the resulting immunized cells are fused to known parent cells by a standard cell fusion technique, and then the fused cells are screened for monoclonal antibody-producing cells (hybridomas) by a standard screening method. Construction of hybridomas can be performed according to the method of e.g. Milstein et al. (Kohler. G. and Milstein, C., Methods Enzymol. (1981) 73: 3-46). If the antigen has low immunogenicity, it can be bound to an immunogenic macromolecule such as albumin and used for immunization.

Recombinant antibodies can be used, which are produced by transforming a host with a suitable vector containing an antibody gene cloned from a hybridoma using genetic engineering techniques (see e.g. Carl, A. K. Borrebaeck, James, W. Larrick, THERAPEUTIC MONOCLONAL ANTIBODIES, Published in the United Kingdom by MACMILLAN PUBLISHERS LTD, 1990). Specifically, the cDNA sequences for the variable regions (V regions) of an antibody are synthesized from mRNA of a hybridoma using a reverse transcriptase. Once DNA sequences encoding the V regions of the antibody of interest have been obtained, they may be linked to the DNA sequences encoding the constant regions (C regions) of the antibody of interest and integrated into an expression vector. Alternatively, the DNA sequences encoding the V regions of the antibody may be integrated into an expression vector containing the DNA sequences for the C regions of the antibody. They are integrated into the expression vector in such a manner that they can be expressed under the control of regulatory regions such as enhancers and promoters. Then, a host cell can be transformed with this expression vector to express the antibody.

In the present invention, recombinant antibodies, i.e. antibodies artificially modified to reduce antigenicity in humans or to attain other purposes, such as chimeric antibodies and humanized antibodies can be used. These modified antibodies can be prepared by known processes. Chimeric antibodies consist of the heavy and light chain variable regions of an antibody from a non-human mammal such as a mouse and the heavy and light chain constant regions of a human antibody and can be obtained by linking the DNA sequences encoding the variable regions of the mouse antibody to the DNA sequences for the constant regions of the human antibody and transforming a host with an expression vector containing the linked sequences to allow it to produce a chimeric antibody.

Humanized antibodies are also called reshaped human antibodies and obtained by grafting the complementarity-determining regions (CDRs) of an antibody from a non-human mammal such as a mouse into the complementarity-determining regions of a human antibody and typical gene recombination techniques for preparing them are also known. Specifically, DNA sequences designed to link the CDRs of a mouse antibody to the framework regions (FRs) of a human antibody are synthesized by PCR from several oligonucleotides prepared to have terminal overlapping regions. The resulting DNA sequences are linked to the DNA sequences encoding the constant regions of the human antibody and then integrated into an expression vector, which is transformed into a host to allow it to produce a reshaped antibody (see European Patent Publication No. EP 239400, International Publication No. WO 96/02576). The FRs of the human antibody linked by the CDRs are selected in such a manner that the complementarity-determining regions form an appropriate antigen-binding site. If necessary, reshaped humanized antibodies may have some amino acid changes in the framework regions of the variable regions so that the complementarity-determining regions form an appropriate antigen-binding site (Sato, K. et al., Cancer Res. (1993) 53, 851-856).

Methods for obtaining human antibodies are also known. For example, a desired human antibody having a binding activity for a desired antigen can be obtained by in vitro immunizing human lymphocytes with the desired antigen or a cell expressing the desired antigen and fusing the immunized lymphocytes to human myeloma cells such as U266 (see JPB No. HEI1-59878). A desired human antibody can also be obtained by immunizing a transgenic animal having all human antibody gene repertoires with an antigen (see International Publications Nos. WO 93/12227, WO 92/03918, WO 94/02602, WO 94/25585, WO 96/34096, WO 96/33735). Methods for obtaining a human antibody by panning using a human antibody library are also known. For example, phages binding to an antigen can be selected by expressing the variable regions of a human antibody as single chain antibody fragments (scFv) on phage surfaces by a phage display method. The DNA sequences encoding the variable regions of the human antibody binding to the antigen can be determined by analyzing the genes of the selected phages. A whole human antibody can be obtained by preparing a suitable expression vector on the basis of the determined DNA sequences of the scFv fragments binding to the antigen.

These methods are already well known from WO 92/01047, WO 92/20791, WO 93/06213, WO 93/11236, WO 93/19172, WO 95/01438, WO 95/15388.

When an antibody is to be prepared by transforming a preliminarily isolated antibody gene into a suitable host, a suitable host can be used in combination with an expression vector. Suitable eukaryotic cells used as hosts include animal cells, plant cells and fungal cells. Known animal cells include (1) mammal cells such as CHO, COS, myeloma, BHK (baby hamster kidney), HeLa and Vero cells; (2) amphibian cells such as Xenopus oocytes; or (3) insect sells such as sf9, sf21 and Tn5. Known plant cells include cells of Nicotiana such as Nicotiana tabacum, which can be used as callus cultures. Known fungal cells include yeasts such as *Saccharomyces* spp., e.g. *Saccharomyces serevisiae* and filamentous fungi such as *Aspergillus* spp., e.g. *Aspergillus niger*. Prokaryotic cells can be used as producing systems using bacterial cells. Known bacterial cells include *E. coli* and *Bacillus subtilis*. Antibodies can be obtained by transforming these cells with an antibody gene of interest and culturing the transformed cells in vitro.

Antibodies contained in stabilized formulations of the present invention include, but not limited to, anti-IL-6 receptor antibodies, anti-HM1.24 antigen monoclonal antibodies, anti-parathyroid hormone related peptide antibodies (anti-PTHrP antibodies), etc.

Preferred reshaped humanized antibodies for use in the present invention include humanized anti-IL-6 receptor antibodies (hPM-1) (see International Publication No. WO92-19759), humanized anti-HM1.24 antigen monoclonal antibodies (see International Publication No. WO98-14580) and humanized anti-parathyroid hormone related peptide antibodies (anti-PTHrP antibodies) (see International Publication No. WO98-13388).

Antibodies contained in solution formulations of the present invention may belong to any immunoglobulin class, preferably IgG such as IgG1, IgG2, IgG3 and IgG4, more preferably IgG1.

Antibody-containing solution formulations in the present invention preferably show no increase in multimers and contain 50 or less insoluble particles per mL after freeze/thaw cycling.

In antibody-containing solutions or solution formulations of the present invention, the formation of dimers during freeze/thaw cycles can be inhibited by adding sugars. The sugars that can be used include nonreducing oligosaccharides, e.g. nonreducing disaccharides such as sucrose and trehalose or nonreducing trisaccharides such as raffinose, and especially preferred are nonreducing oligosaccharides. Preferred nonreducing oligosaccharides are nonreducing disaccharides, more preferably sucrose and trehalose.

In antibody-containing solutions or solution formulations of the present invention, the formation of multimers and degradation products during long-term storage can be inhibited by adding sugars. The sugars that can be used include sugar alcohols such as mannitol and sorbitol; and nonreducing oligosaccharides, e.g. nonreducing disaccharides such as sucrose and trehalose or nonreducing trisaccharides such as raffinose, among which nonreducing oligosaccharides are especially preferred. Preferred nonreducing oligosaccharides are nonreducing disaccharides, more preferably sucrose and trehalose.

The sugars should be added at 0.1-500 mg/mL, preferably 10-300 mg/mL, more preferably 25-100 mg/mL.

In the present invention, the formation of insoluble particles during freeze/thaw cycles of antibody-containing solution formulations can be very remarkably inhibited by adding surfactants. Typical examples of surfactants include:

nonionic surfactants, e.g., sorbitan fatty acid esters such as sorbitan monocaprylate, sorbitan monolaurate, sorbitan monopalmitate; glycerin fatty acid esters such as glycerin monocaprylate, glycerin monomyristate, glycerin monostearate; polyglycerin fatty acid esters such as decaglyceryl monostearate, decaglyceryl distearate, decaglyceryl monolinoleate; polyoxyethylene sorbitan fatty acid esters such as polyoxyethylene sorbitan monolaurate, polyoxyethylene sorbitan monooleate, polyoxyethylene sorbitan monostearate, polyoxyethylene sorbitan monopalmitate, polyoxyethylene sorbitan trioleate, polyoxyethylene sorbitan tristearate; polyoxyethylene sorbitol fatty acid esters such as polyoxyethylene sorbitol tetrastearate, polyoxyethylene sorbitol tetraoleate; polyoxyethylene glycerin fatty acid esters such as polyoxyethylene glyceryl monostearate; polyethylene glycol fatty acid esters such as polyethylene glycol distearate; polyoxyethylene alkyl ethers such as polyoxyethylene lauryl ether; polyoxyethylene polyoxypropylene alkyl ethers such as polyoxyethylene polyoxypropylene glycol ether, polyoxyethylene polyoxypropylene propyl ether, polyoxyethylene polyoxypropylene cetyl ether; polyoxyethylene alkyl phenyl ethers such as polyoxyethylene nonyl phenyl ether; polyoxyethylene hardened castor oils such as polyoxyethylene castor oil, polyoxyethylene hardened castor oil (polyoxyethylene hydrogenated castor oil); polyoxyethylene beeswax derivatives such as polyoxyethylene sorbitol beeswax; polyoxyethylene lanolin derivatives such as polyoxyethylene lanolin; polyoxyethylene fatty acid amides such as polyoxyethylene stearic acid amide having an HLB of 6-18;

anionic surfactants, e.g., alkyl sulfates having a C10-18 alkyl group such as sodium cetyl sulfate, sodium lauryl sulfate, sodium oleyl sulfate; polyoxyethylene alkyl ether sulfates having an average EO mole number of 2-4 and a C10-18 alkyl group such as sodium polyoxyethylene lauryl sulfate; alkyl sulfosuccinic acid ester salts having a C8-18 alkyl group such as sodium laurylsulfosuccinate; and natural surfactants, e.g., lecithin; glycerophospholipids; sphingophospholipids such as sphingomyelin; sucrose fatty acid esters of C12-18 fatty acids. Formulations of the present invention can contain one or more of these surfactants in combination. Preferred surfactants for use in solution formulations of the present invention are polyoxyethylene sorbitan fatty acid esters such as Polysorbate 20, 40, 60 or 80, especially Polysorbates 20 and 80. Polyoxyethylene polyoxypropylene glycols such as poloxamers (e.g. Pluronic® F-68) are also preferred.

The amount of surfactants to be added varies with the type of the particular surfactant used, but it is typically 0.001-100 mg/mL, preferably 0.003-50 mg/mL, more preferably 0.005-2 mg/mL in the case of Polysorbate 20 or Polysorbate 80.

Preferably, antibody-containing solution formulations of the present invention are substantially free from proteins such as human serum albumin or purified gelatin as stabilizers.

Antibody formulations of the present invention preferably have a pH of 4-8, more preferably 5-7, still more preferably 6-6.5. However, the pH depends on the antibody contained and is not limited to these values.

Formulations of the present invention may further contain isotonizing agents, e.g., polyethylene glycol; and sugars such as dextran, mannitol, sorbitol, inositol, glucose, fructose, lactose, xylose, mannose, maltose, sucrose, trehalose and raffinose.

Antibody-containing solution formulations of the present invention may further contain diluents, solubilizing agents, excipients, pH-modifiers, soothing agents, buffers, sulfur-containing reducing agents, antioxidants or the like, if desired. For example, sulfur-containing reducing agents include N-acetylcysteine, N-acetylhomocysteine, thioctic acid, thiodiglycol, thioethanolamine, thioglycerol, thiosorbitol, thioglycolic acid and salts thereof, sodium thiosulfate, glutathione, and sulfhydryl-containing compounds such as thioalkanoic acid having 1 to 7 carbon atoms. Antioxidants include erythorbic acid, dibutylhydroxytoluene, butylhydroxyanisole, α-tocopherol, tocopherol acetate, L-ascorbic acid and salts thereof, L-ascorbyl palmitate, L-ascorbyl stearate, sodium bisulfite, sodium sulfite, triamyl gallate, propyl gallate or chelating agents such as disodium ethylenediamine tetraacetate (EDTA), sodium pyrophosphate and sodium metaphosphate. Other common additives may also be contained, e.g., inorganic salts such as sodium chloride, potassium chloride, calcium chloride, sodium phosphate, potassium phosphate and sodium bicarbonate; and organic salts such as sodium citrate, potassium citrate and sodium acetate.

Formulations of the present invention can be prepared by dissolving these components in an aqueous buffer known in the field of solution formulations such as a phosphate buffer (preferably sodium monohydrogen phosphate—sodium dihydrogen phosphate system) and/or a citrate buffer (preferably sodium citrate buffer) and/or an acetate buffer to prepare a solution formulation. The concentration of the buffer is typically 1-500 mM, preferably 5-100 mM, more preferably 10-20 mM.

Antibody-containing solution formulations of the present invention are normally administered via parenteral routes such as injection (e.g. subcutaneous, intravenous, intramuscular or intraperitoneal injection) or percutaneous, mucosal, nasal or pulmonary administration, but may also be orally administered.

Antibody-containing solution formulations of the present invention can be normally supplied in sealed and sterilized plastic or glass containers having a defined volume such as vials, ampules or syringes or a large volume such as bottles. In terms of convenience, prefilled syringes are preferred.

The amount of antibodies contained in formulations of the present invention is typically 0.1-200 mg/ml, preferably 1-120 mg/ml, more preferably 2-22.5 mg/mL, depending on the type of the disease to be treated, the severity of the disease, the age of the patient and other factors.

In solution formulations of the present invention, the formation of insoluble particles especially during freeze/thaw cycles could be remarkably inhibited and the formation of insoluble matters during long-term stability tests could also be remarkably inhibited by adding surfactants, as shown in the examples below. It was also found that the formation of multimers such as dimers as well as the formation of degradation products could be remarkably inhibited and remaining antibody monomer contents could be increased by adding sugars.

The following examples further illustrate the present invention without, however, limiting the scope of the invention thereto. Various changes and modifications can be made by those skilled in the art on the basis of the description of the invention, and such changes and modifications are also included in the present invention.

EXAMPLES

Antibody Samples

An hPM-1 antibody was used as a humanized anti-IL-6 receptor antibody. The hPM-1 antibody was a humanized hPM-1 antibody prepared by the method described in Reference example 2 of JPA HEI 8-99902 using the human elongation factor Iα promoter described in Example 10 of International Patent Publication No. WO92/19759.

An antibody prepared by the method described in Reference example 2 of International Patent Publication No. WO98-35698 (hereinafter referred to as anti-HM1.24 antibody) was used as a humanized anti-HM1.24 antigen monoclonal antibody.

The hPM-1 antibody and anti-HM1.24 antibody used in the following examples are both IgG1 class antibodies.

Test Methods (A) Tests on hPM-1 antibody (1) Gel permeation chromatography (GPC)

Each sample is diluted with the mobile phase to contain hPM-1 in an amount equivalent to about 1 mg in 1 mL and tested under the following HPLC conditions in 30-60 μL.

Column: TSK gel G3000SW$_{XL}$ (TOSOH)
Guard column: TSK guard column SW$_{XL}$ (TOSOH)
Column temperature: constant around 25° C.
Mobile phase: 50 mM phosphate buffer (pH 7.0)-300 mM sodium chloride
Flow rate: about 1.0 mL/min
Measured at wavelength: 280 nm.

The peak area was determined by automatic integration to calculate the hPM-1 content from the peak area of a standard hPM-1 product and the remaining hPM-1 percentage from the initial evaluation results using the following equations.

$$hPM\text{-}1 \text{ content (mg/mL)} = \frac{\text{Concentration of standard } hPM\text{-}1 \text{ product} \times \text{Peak area of test sample}}{\text{Peak area of standard } hPM\text{-}1 \text{ product}}$$

$$\text{Remaining } hPM\text{-}1 \text{ percentage (\%)} = \frac{hPM\text{-}1 \text{ content after thermal acceleration and freeze/thaw cycles}}{\text{Initial } hPM\text{-}1 \text{ content}} \times 100$$

The percentages of dimers, other multimers and degradation products were calculated by the area percentage method using the following equation.

$$\text{Dimers (or other multimers or degradation products) (\%)} = \frac{\text{Peak area of dimers (or other multimers or degradation products)}}{\text{Total peak area}} \times 100$$

(2) Evaluation of the number of insoluble particles by a light obscuration automatic particle counter (HIAC)

Evaluation was made according to the method using an automatic light obscuration particle counter as described in the section of Insoluble Particulate Matter Test for Injections in the part of General Tests, Processes and Apparatus in the Japanese Pharmacopoeia.

(3) Automated visual inspection

Automated visual inspection was performed according to the method as described in the section of Foreign Insoluble Matter Test for Injections in the part of General Tests, Processes and Apparatus in the Japanese Pharmacopoeia.

Visual inspection system: Type E422 (Eisai).

(B) Tests on anti-HM1.24 antibody (1) Gel permeation chromatography (GPC); measured at N=3 to evaluate the remaining percentage (%) to the initial content and also evaluate multimers and degradation products in percentages.

Column: TSK gel G3000SW$_{XL}$ (TOSOH)
Guard column: TSK guard column SW$_{XL}$ (TOSOH)
Column temperature: constant around 25° C.
Mobile phase: 50 mM phosphate buffer (pH 7.0)-300 mM sodium chloride
Flow rate: about 0.5 mL/min
Measured at wavelength: 280 nm Method for Calculating the Concentration $$\text{Anti-}HM1.24 \text{ antibody content (mg/mL)} = \frac{\text{Concentration of standard} \times \text{Peak area of anti-}HM1.24 \text{ antibody} \times \text{Amount of standard applied}}{\text{Total peak area of standard} \times \text{Amount of test sample applied}}$$

$$\text{Remaining anti-}HM1.24 \text{ antibody percentage (\%)} = \frac{\text{Anti-}HM1.24 \text{ antibody content after thermal acceleration}}{\text{Initial anti-}HM1.24 \text{ antibody content}} \times 100$$

The percentages of multimers and degradation products were calculated by the area percentage method.

$$\text{Multimers (or degradation products) (\%)} = \frac{\text{Peak area of multimers (or degradation products)}}{\text{Total peak area}} \times 100$$

Example 1

Effects of Adding A Surfactant (1)

The influence of a surfactant (Polysorbate 80) on heat stability and freeze/thaw stability was tested. Samples containing Polysorbate 80 at various concentrations shown in Table 1 were prepared and tested as follows.

(1) Stability to thermal acceleration (50° C.-2W) was evaluated from the remaining hPM-1 percentage and the formation of multimers and degradation products as determined by gel permeation chromatography (GPC). The number of insoluble particles per mL was measured by an automatic light obscuration particle counter (HIAC).

(2) Stability to freeze/thaw cycling (3 cycles of storage at −20° C. for 3 days and then 5° C. for one day) was evaluated from the remaining hPM-1 percentage and the formation of multimers and degradation products as determined by gel permeation chromatography (GPC). The number of insoluble particles per mL was measured by an automatic light obscuration particle counter (HIAC).

The results obtained are shown in Table 1.

TABLE 1

<Test samples and results>

|  |  | Sample 1 | Sample 2 | Sample 3 | Sample 4 |
|---|---|---|---|---|---|
| hPM-1 (mg/mL) |  | 20 | 20 | 20 | 20 |
| Polysorbate 80 (mg/mL) |  | 0 | 0.25 | 0.5 | 0.75 |
| Sodium Phosphate (mM) |  | 15 | 15 | 15 | 15 |
| pH |  | 6.5 | 6.5 | 6.5 | 6.5 |
| Initial | hPM-1 content (mg/mL) | 20.1 | 20.3 | 20.3 | 20.4 |
|  | Dimers (%) | 0.21 | 0.22 | 0.22 | 0.23 |
|  | Other multimers (%) | 0 | 0 | 0 | 0 |
|  | Degradation products (%) | 0 | 0 | 0 | 0 |
|  | Number of particles of 10 μm or more (particles/mL) | 0 | 0 | 2 | 0 |
|  | Number of particles of 25 μm or more (particles/mL) | 0 | 0 | 0 | 0 |
| Thermal acceleration (50° C.-2 W) | Remaining hPM-1 (%) | 99.4 | 98.2 | 98.1 | 98.0 |
|  | Dimers (%) | 1.38 | 1.39 | 1.39 | 1.41 |
|  | Other multimers (%) | 0 | 0 | 0 | 0 |
|  | Degradation products (%) | 0.91 | 0.91 | 0.90 | 0.90 |
|  | Number of particles of 10 μm or more (particles/mL) | 0 | 0 | 0 | 0 |
|  | Number of particles of 25 μm or more (particles/mL) | 0 | 0 | 0 | 0 |
| Freeze/thaw (−20° C.→5° C., 3 cycles) | Remaining hPM-1 (%) | 99.7 | 99.6 | 99.4 | 99.3 |
|  | Dimers (%) | 0.60 | 0.56 | 0.52 | 0.49 |
|  | Other multimers (%) | 0 | 0 | 0 | 0 |
|  | Degradation products (%) | 0 | 0 | 0 | 0 |
|  | Number of particles of 10 μm or more (particles/mL) | 3287 | 7 | 1 | 4 |

TABLE 1-continued

<Test samples and results>

|  | Sample 1 | Sample 2 | Sample 3 | Sample 4 |
|---|---|---|---|---|
| Number of particles of 25 μm or more (particles/mL) | 539 | 3 | 0 | 0 |

It was found that the formation of insoluble particles during freeze/thaw cycles is remarkably inhibited by the addition of Polysorbate 80. No significant variation in stability with the concentration of Polysorbate 80 was found.

Example 2

Effects of Adding A Surfactant (2)

The influence of a surfactant (Polysorbate 80) on stability to freeze/thaw cycling and shaking was tested. Samples containing Polysorbate 80 at various concentrations shown in Table 2 were prepared and tested as follows.

Stability to freeze/thaw cycling (2 cycles of storage at −20° C. for 8 hours and then 5° C. for 8 hours) was evaluated from the number of insoluble particles per mL as measured by an automatic light obscuration particle counter (HIAC). The presence or absence of insoluble matters was evaluated by automated visual inspection.

The results obtained are shown in Table 2.

TABLE 2

<Test samples and results>

|  |  | Sample 5 | Sample 6 | Sample 7 | Sample 8 | Sample 9 | Sample 10 |
|---|---|---|---|---|---|---|---|
| hPM-1 (mg/mL) |  | 20 | 20 | 20 | 20 | 20 | 20 |
| Polysorbate 80 (mg/mL) |  | 0 | 0.005 | 0.05 | 0.25 | 0.5 | 0.75 |
| Sucrose (mg/mL) |  | 50 | 50 | 50 | 50 | 50 | 50 |
| Sodium Phosphate (mM) |  | 15 | 15 | 15 | 15 | 15 | 15 |
| pH |  | 6.5 | 6.5 | 6.5 | 6.5 | 6.5 | 6.5 |
| Initial | Number of particles of 10 μm or more (particles/mL) | 10 | 0 | 0 | 0 | 0 | 0 |
|  | Number of particles of 25 μm or more (particles/mL) | 2 | 0 | 0 | 0 | 0 | 0 |
|  | Insoluble matters | Yes | No | No | No | No | No |
| Freeze/thaw (−20° C.→5° C., 2 cycles) | Number of particles of 10 μm or more (particles/mL) | 7020 | 8 | 0 | 0 | 0 | 1 |
|  | Number of particles of 25 μm or more (particles/mL) | 601 | 0 | 0 | 0 | 0 | 0 |
|  | Insoluble matters | Yes | Yes | No | No | No | No |

It was found that the formation of insoluble particles and insoluble matters during freeze/thaw cycles is remarkably inhibited by the addition of Polysorbate 80. The effect against the formation of insoluble matters was found to be dependent on the concentration of Polysorbate 80.

Example 3

Effects of Adding Sugars

The influence of adding sugars on freeze/thaw stability was tested. Samples containing various sugars shown in Table 3 (sucrose, mannitol, trehalose) were prepared and evaluated for stability to freeze/thaw cycling (22 cycles of storage at −20° C. for 2 hours and then 5° C. for 2 hours) as determined by gel permeation chromatography (GPC) from the amount of dimers formed.

TABLE 3

<Test samples and results>

|  |  | Sample 11 | Sample 12 | Sample 13 | Sample 14 | Sample 15 |
|---|---|---|---|---|---|---|
| hPM-1 (mg/mL) | | 20 | 20 | 20 | 20 | 20 |
| Sucrose (mg/mL) | | 0 | 50 | 0 | 0 | 0 |
| Mannitol (mg/mL) | | 0 | 0 | 50 | 94 | 0 |
| Trehalose (mg · mL) | | 0 | 0 | 0 | 0 | 50 |
| Polysorbate 80 (mg/mL) | | 0.5 | 0.5 | 0.5 | 0.5 | 0.5 |
| Sodium Phosphate (mM) | | 15 | 15 | 15 | 15 | 15 |
| pH | | 6.5 | 6.5 | 6.5 | 6.5 | 6.5 |
| Initial | Dimers (%) | 0.42 | 0.43 | 0.41 | 0.38 | 0.42 |
| Freeze/thaw (−20° C.→5° C., 22 cycles) | Dimers (%) | 0.67 | 0.43 | 0.89 | 2.60 | 0.41 |

It was found that the formation of dimers is inhibited by the addition of sucrose and trehalose.

Example 4

Influence of Sucrose on Heat Stability and Freeze/Thaw Stability

The influence of sucrose on heat stability and freeze/thaw stability was tested. Samples containing sucrose at various concentrations shown in Table 4 were prepared and tested as follows.

(1) Stability to thermal acceleration (50° C.-2W) was evaluated from the remaining hPM-1 percentage and the formation of multimers and degradation products as determined by gel permeation chromatography (GPC). The number of insoluble particles per mL was measured by an automatic light obscuration particle counter (HIAC).

(2) Stability to freeze/thaw cycling (3 cycles of storage at −20° C. for 3 days and then 5° C. for one day) was evaluated from the remaining hPM-1 percentage and the formation of multimers and degradation products as determined by gel permeation chromatography (GPC). The number of insoluble particles per mL was measured by an automatic light obscuration particle counter (HIAC).

The results obtained are shown in Table 4.

TABLE 4

<Test samples and results>

|  |  | Sample 16 | Sample 17 | Sample 18 | Sample 19 |
|---|---|---|---|---|---|
| hPM-1 (mg/mL) | | 20 | 20 | 20 | 20 |
| Sucrose (mg/mL) | | 0 | 25 | 50 | 100 |
| Polysorbate 80 (mg/mL) | | 0.5 | 0.5 | 0.5 | 0.5 |
| Sodium Phosphate (mM) | | 15 | 15 | 15 | 15 |
| pH | | 6.5 | 6.5 | 6.5 | 6.5 |
| Initial | hPM-1 content (mg/mL) | 19.2 | 19.2 | 19.3 | 19.3 |
| | Dimers (%) | 0.18 | 0.16 | 0.15 | 0.15 |
| | Other multimers (%) | 0 | 0 | 0 | 0 |
| | Degradation products (%) | 0 | 0 | 0 | 0 |
| | Number of particles of 10 μm or more (particles/mL) | 0 | 0 | 12 | 0 |
| | Number of particles of 25 μm or more (particles/mL) | 0 | 0 | 1 | 0 |
| Thermal acceleration (50° C.-2 W) | Remaining hPM-1 (%) | 98.2 | 98.5 | 97.8 | 97.8 |
| | Dimers (%) | 1.37 | 1.47 | 1.36 | 1.41 |
| | Other multimers (%) | 0 | 0 | 0 | 0 |
| | Degradation products (%) | 0.92 | 0.89 | 0.89 | 0.89 |
| | Number of particles of 10 μm or more (particles/mL) | 0 | 0 | 0 | 0 |
| | Number of particles of 25 μm or more (particles/mL) | 0 | 0 | 0 | 0 |
| Freeze/thaw (−20° C.→5° C., 3 cycles) | Remaining hPM-1 (%) | 100.2 | 100.8 | 100.4 | 100.2 |
| | Dimers (%) | 0.36 | 0.18 | 0.17 | 0.15 |
| | Other multimers (%) | 0 | 0 | 0 | 0 |
| | Degradation products (%) | 0 | 0 | 0 | 0 |
| | Number of particles of 10 μm or more (particles/mL) | 1 | 3 | 5 | 2 |

TABLE 4-continued

<Test samples and results>

|  | Sample 16 | Sample 17 | Sample 18 | Sample 19 |
|---|---|---|---|---|
| Number of particles of 25 μm or more (particles/mL) | 1 | 0 | 0 | 0 |

It was found that the formation of dimers during freeze/thaw cycles is remarkably inhibited by the addition of sucrose. No variation in stability with the concentration of sucrose was found.

Example 5

Influence of Antibody Concentration

The influence of the concentration of hPM-1 on heat stability was tested. Samples containing hPM-1 at various concentrations shown in Table 5 were prepared and tested as follows.

Stability to thermal acceleration (50° C.-2W) was evaluated from the remaining hPM-1 percentage and the formation of multimers and degradation products as determined by gel permeation chromatography (GPC). The number of insoluble particles per mL was measured by an automatic light obscuration particle counter (HIAC).

The results obtained are shown in Table 5.

TABLE 5

<Test samples and results>

|  |  | Sample 20 | Sample 21 | Sample 22 |
|---|---|---|---|---|
| hPM-1(mg/mL) |  | 17.5 | 20 | 22.5 |
| Sucrose (mg/mL) |  | 50 | 50 | 50 |
| Polysorbate 80(mg/mL) |  | 0.5 | 0.5 | 0.5 |
| Sodium Phosphate(mM) |  | 15 | 15 | 15 |
| pH |  | 6.5 | 6.5 | 6.5 |
| Initial | hPM-1 content (mg/mL) | 17.0 | 19.3 | 21.4 |
|  | Dimers (%) | 0.16 | 0.16 | 0.18 |
|  | Other multimers (%) | 0 | 0 | 0 |
|  | Degradation products (%) | 0 | 0 | 0 |
|  | Number of particles of 10 μm or more (particles/mL) | 0 | 0 | 0 |
|  | Number of particles of 25 μm or more (particles/mL) | 0 | 0 | 0 |
| Thermal acceleration (50° C.-2 W) | Remaining hPM-1 (%) | 99.6 | 100.2 | 99.8 |
|  | Dimers (%) | 1.26 | 1.35 | 1.45 |
|  | Other multimers (%) | 0 | 0 | 0 |
|  | Degradation products (%) | 0.95 | 0.93 | 0.99 |
|  | Number of particles of 10 μm or more (particles/mL) | 0 | 3 | 0 |
|  | Number of particles of 25 μm or more (particles/mL) | 0 | 0 | 0 |

No variation in stability with the concentration of hPM-1 was found.

Example 6

Influence of the Concentration of Phosphate Buffer

The influence of the concentration of phosphate buffer on heat stability was tested. Samples containing phosphate buffer at various concentrations shown in Table 6 were prepared and tested as follows.

Stability to thermal acceleration (50° C.-2W) was evaluated from the remaining hPM-1 percentage and the formation of multimers and degradation products as determined by gel permeation chromatography (GPC). The number of insoluble particles per mL was measured by an automatic light obscuration particle counter (HIAC).

The results obtained are shown in Table 6.

TABLE 6

<Test samples and results>

|  |  | Sample 23 | Sample 24 | Sample 25 |
|---|---|---|---|---|
| hPM-1(mg/mL) |  | 20 | 20 | 20 |
| Sucrose (mg/mL) |  | 50 | 50 | 50 |
| Polysorbate 80(mg/mL) |  | 0.5 | 0.5 | 0.5 |
| Sodium Phosphate(mM) |  | 10 | 15 | 20 |
| pH |  | 6.5 | 6.5 | 6.5 |
| Initial | hPM-1 content (mg/mL) | 19.3 | 19.4 | 19.4 |
|  | Dimers (%) | 0.17 | 0.18 | 0.18 |
|  | Other multimers (%) | 0 | 0 | 0 |
|  | Degradation products (%) | 0 | 0 | 0 |
|  | Number of particles of 10 μm or more (particles/mL) | 0 | 0 | 0 |
|  | Number of particles of 25 μm or more (particles/mL) | 0 | 0 | 0 |
| Thermal acceleration (50° C.-2 W) | Remaining hPM-1 (%) | 100.1 | 99.0 | 99.2 |
|  | Dimers (%) | 1.37 | 1.43 | 1.45 |
|  | Other multimers (%) | 0 | 0 | 0 |
|  | Degradation products (%) | 0.94 | 0.95 | 0.94 |
|  | Number of particles of 10 μm or more (particles/mL) | 0 | 0 | 0 |
|  | Number of particles of 25 μm or more (particles/mL) | 0 | 0 | 0 |

No variation in stability with the concentration of phosphate buffer was found.

Example 7

Effects of Adding Sugars

Heat stability tests were performed to evaluate the effects of adding a sugar (sucrose or mannitol) at anti-HM1.24 antibody concentrations in the range of 2.5-10 mg/mL. Samples containing the sugar at various concentrations in low and high anti-HM1.24 antibody preparations (1 mL/5 mL vial) and determined for the remaining percentage (%), multimers (%) and degradation products (%) under various storage conditions (60° C.-1W, 50° C.-3M, 5° C.-6M, Initial).

Test formulations of low-concentration preparations and the results are shown in Tables 7 and 8, while test formulations of high-concentration preparations and the results are shown in Tables 9 and 10.

TABLE 7

|  | Sample 26 | Sample 27 | Sample 28 | Sample 29 | Sample 30 | Sample 31 | Sample 32 |
|---|---|---|---|---|---|---|---|
| Anti-H.M1.24 antibody (mg/mL) | 2.5 | 2.5 | 2.5 | 2.5 | 2.5 | 2.5 | 2.5 |
| Sucrose (mg/mL) | 10 | 50 | 100 | — | — | — | — |
| Mannitol (mg/mL) | — | — | — | 10 | 50 | 100 | — |
| NaCl (mM) | 100 | 100 | 100 | 100 | 100 | 100 | 100 |
| pH | 6.0 | 6.0 | 6.0 | 6.0 | 6.0 | 6.0 | 6.0 |

TABLE 8

|  | Remaining percentage (%) | Multimers (%) | Degradation products (%) |
|---|---|---|---|
| 60° C.-1W |  |  |  |
| Sample 26 | 90.9% | 5.06% | 1.99% |
| Sample 27 | 91.1% | 4.60% | 1.98% |
| Sample 28 | 90.0% | 4.14% | 2.05% |
| Sample 29 | 85.5% | 5.04% | 2.20% |
| Sample 30 | 90.3% | 4.99% | 1.99% |
| Sample 31 | 86.6% | 5.57% | 2.63% |
| Sample 32 | 88.9% | 5.39% | 2.09% |
| 50° C.-3M |  |  |  |
| Sample 26 | 77.0% | 14.0% | 6.98% |
| Sample 27 | 81.5% | 13.7% | 6.46% |
| Sample 28 | 84.9% | 12.9% | 4.83% |
| Sample 29 | 78.9% | 14.3% | 7.31% |
| Sample 30 | 75.2% | 13.2% | 6.72% |
| Sample 31 | 76.1% | 12.7% | 6.24% |
| Sample 32 | 76.8% | 15.5% | 7.62% |
| 5° C.-6M |  |  |  |
| Sample 26 | 103.8% | 3.82% | 0.00% |
| Sample 27 | 104.0% | 3.44% | 0.00% |
| Sample 28 | 104.2% | 3.43% | 0.00% |
| Sample 29 | 103.8% | 3.49% | 0.00% |
| Sample 30 | 104.3% | 3.46% | 0.00% |
| Sample 31 | 104.3% | 3.45% | 0.00% |
| Sample 32 | 103.5% | 3.49% | 0.00% |
| Initial |  |  |  |
| Sample 26 | 100.0% | 3.73% | 0.00% |
| Sample 27 | 100.0% | 3.34% | 0.00% |
| Sample 28 | 100.0% | 3.34% | 0.00% |
| Sample 29 | 100.0% | 3.38% | 0.00% |
| Sample 30 | 100.0% | 3.36% | 0.00% |
| Sample 31 | 100.0% | 3.36% | 0.00% |
| Sample 32 | 100.0% | 3.38% | 0.00% |

After thermal acceleration at 50° C.-3M, the samples showed an increase in the remaining antibody monomer percentage and a decrease in the formation of multimers and degradation products in a manner dependent on the concentration of sucrose added. After acceleration at 60° C.-1W, the samples also showed a decrease in the amount of multimers formed. Under acceleration at 50° C.-3M, the effect of sugar addition on the remaining antibody percentage was more remarkable with sucrose than mannitol. The effect of sugar addition on the inhibition of association was also found with mannitol.

TABLE 9

|  | Sample 33 | Sample 34 | Sample 35 | Sample 36 | Sample 37 | Sample 38 |
|---|---|---|---|---|---|---|
| Anti-H.M1.24 antibody (mg/mL) | 2.5 | 5.0 | 5.0 | 10 | 10 | 10 |
| Polysorbate 80 (%) | 0.025 | 0.025 | 0.025 | 0.025 | 0.025 | 0.025 |
| Acetate (mM) | 20 | 20 | 20 | 20 | 20 | 20 |
| NaCl (mM) | 100 | 100 | 100 | 100 | 100 | 100 |
| pH | 6.0 | 6.0 | 6.0 | 6.0 | 6.0 | 6.0 |
| Sucrose (mg/mL) | 10 | 10 | 20 | 10 | 40 | 0 |

TABLE 10

|  | Remaining percentage (%) | Multimers (%) | Degradation products (%) |
|---|---|---|---|
| 60° C.-1W |  |  |  |
| Sample 33 | 96.6% | 4.78% | 2.16% |
| Sample 34 | 96.1% | 6.47% | 1.84% |
| Sample 35 | 96.1% | 6.33% | 1.84% |
| Sample 36 | 96.1% | 6.66% | 1.76% |
| Sample 37 | 97.0% | 5.96% | 1.75% |
| Sample 38 | 95.3% | 7.11% | 1.82% |
| 50° C.-1M |  |  |  |
| Sample 33 | 94.6% | 5.01% | 2.12% |
| Sample 34 | 95.9% | 5.62% | 2.06% |
| Sample 35 | 95.9% | 5.27% | 2.09% |
| Sample 36 | 96.7% | 5.37% | 1.97% |

TABLE 10-continued

|  | Remaining percentage (%) | Multimers (%) | Degradation products (%) |
|---|---|---|---|
| Sample 37 | 97.1% | 4.95% | 1.96% |
| Sample 38 | 95.5% | 5.69% | 2.02% |
| 5° C.-6M |  |  |  |
| Sample 33 | 107.8% | 3.50% | 0.00% |
| Sample 34 | 106.1% | 3.52% | 0.00% |
| Sample 35 | 106.1% | 3.51% | 0.00% |
| Sample 36 | 104.0% | 3.59% | 0.00% |
| Sample 37 | 104.1% | 3.57% | 0.00% |
| Sample 38 | 103.7% | 3.61% | 0.00% |
| Initial |  |  |  |
| Sample 33 | 100.0% | 3.40% | 0.00% |
| Sample 34 | 100.0% | 3.36% | 0.00% |
| Sample 35 | 100.0% | 3.36% | 0.00% |
| Sample 36 | 100.0% | 3.38% | 0.00% |
| Sample 37 | 100.0% | 3.37% | 0.00% |
| Sample 38 | 100.0% | 3.39% | 0.00% |

Comparison of the amounts of multimers formed after thermal acceleration showed that association is inhibited better as the concentration of sucrose added increases at the same concentration of anti-HM1.24 antibody. It was found that sucrose also contributes to the inhibition of association in high concentration anti-HM1.24 antibody formulations.

Example 8

Effects of Sugar Addition

Effects of sucrose addition were further tested at various amounts. Samples shown in Table 11 were prepared and stored at 50° C.-1M, after which the remaining monomer antibody percentage and the amount of multimers were determined by GPC. The results obtained are shown in Table 12.

TABLE 11

|  | Sample 39 | Sample 40 | Sample 41 | Sample 42 |
|---|---|---|---|---|
| Anti-H.M1.24 antibody (mg/mL) | 10 | 10 | 10 | 10 |
| Polysorbate 80 (%) | 0.05 | 0.05 | 0.05 | 0.05 |
| Acetate (mmol/L) | 10 | 10 | 10 | 10 |
| NaCl (mmol/L) | 100 | 100 | 100 | 100 |
| pH | 6.0 | 6.0 | 6.0 | 6.0 |
| Sucrose (mg/mL) | 0 | 25 | 50 | 75 |

TABLE 12

|  | Remaining percentage (%) | | Multimers (%) | |
|---|---|---|---|---|
|  | Initial | 50° C.-1M | Initial | 50° C.-1M |
| Sample 39 | 100.0% | 83.3% | 3.6% | 12.2% |
| Sample 40 | 100.0% | 86.4% | 3.6% | 9.7% |
| Sample 41 | 100.0% | 87.8% | 3.5% | 8.4% |
| Sample 42 | 100.0% | 87.2% | 3.5% | 8.9% |

It was found that sucrose is effective for inhibiting the formation of multimers of anti-HM1.24 antibody.

Example 9

Effects of Adding Sugars (Freeze/Thaw Test)

The influence of adding sugars (nonreducing disaccharides and nonreducing trisaccharides) on freeze/thaw stability was tested. Samples containing sugars shown in Table 13 were prepared and subjected to a freeze/thaw test under the following conditions.

Stability to freeze/thaw cycling was evaluated from the formation of dimers (multimers) as determined by gel permeation chromatography (GPC).

<Test conditions>

| Thaw: −20° C. → 5° C. (1 hour) | Hold: 5° C. (6 hours) |
|---|---|
| Freeze: 5° C. → −20° C. (1 hour) | −20° C. (16 hours) |

The above temperature cycle was repeated 3, 7 and 21 times.

TABLE 13

<Test samples and results>

|  |  | Sample 43 | Sample 44 | Sample 45 | Sample 46 |
|---|---|---|---|---|---|
| hPM-1 (mg/mL) |  | 20 | 20 | 20 | 20 |
| Polysorbate 80 (mg/mL) |  | 0.5 | 0.5 | 0.5 | 0.5 |
| Sodium Phosphate (mM) |  | 15 | 15 | 15 | 15 |
| pH |  | 6.5 | 6.5 | 6.5 | 6.5 |
| Additive (mM) |  | — | Sucrose 145 | Trehalose 145 | Raffinose 145 |
| Initial | Dimers (%) | 0.4 | 0.4 | 0.4 | 0.4 |
|  | Other multimers (%) | N.D. | N.D. | N.D. | N.D. |
|  | Total amount of multimers (%) | 0.4 | 0.4 | 0.4 | 0.4 |
| 3 freeze/thaw cycles | Dimers (%) | 0.7 | 0.4 | 0.5 | 0.8 |
|  | Other multimers (%) | N.D. | N.D. | N.D. | N.D. |
|  | Total amount of multimers (%) | 0.7 | 0.4 | 0.5 | 0.8 |
| 7 freeze/thaw cycles | Dimers (%) | 0.8 | 0.5 | 0.4 | 1.0 |
|  | Other multimers (%) | N.D. | N.D. | N.D. | N.D. |
|  | Total amount of multimers (%) | 0.8 | 0.5 | 0.4 | 1.0 |
| 21 freeze/thaw cycles | Dimers (%) | 1.0 | 0.4 | 0.5 | 1.3 |
|  | Other multimers (%) | N.D. | N.D. | N.D. | N.D. |
|  | Total amount of multimers (%) | 1.0 | 0.4 | 0.5 | 1.3 |

These results showed that the formation of dimers of hPM-1 antibody during freeze/thaw cycles can be remarkably inhibited by adding nonreducing disaccharides (sucrose, trehalose).

Example 10

Effects of Adding Sugars (Heat Stress Test)

The influence of adding sugars (nonreducing disaccharides and nonreducing trisaccharides) on stability during thermal loading was tested. Samples containing sugars shown in Tables 14 and 15 were prepared and subjected to a heat stress test under the following conditions.

Stability during thermal loading was evaluated from the formation of dimers and multimers as determined by gel permeation chromatography (GPC).

TABLE 14

<Test samples and results>

| | | Sample 47 | Sample 48 | Sample 49 | Sample 50 |
|---|---|---|---|---|---|
| hPM-1 (mg/mL) | | 20 | 20 | 20 | 20 |
| Polysorbate 80 (mg/mL) | | 0.5 | 0.5 | 0.5 | 0.5 |
| Sodium Phosphate (mM) | | 15 | 15 | 15 | 15 |
| pH | | 6.5 | 6.5 | 6.5 | 6.5 |
| Additive (mM) | | — | Sucrose 145 | Trehalose 145 | Raffinose 145 |
| Initial | Dimers (%) | 0.4 | 0.4 | 0.4 | 0.4 |
| | Other multimers (%) | N.D. | N.D. | N.D. | N.D. |
| | Total amount of multimers (%) | 0.4 | 0.4 | 0.4 | 0.4 |
| Heat stress test | Dimers (%) | 5.2 | 6.0 | 5.6 | 6.9 |
| | Other multimers (%) | 6.1 | 4.5 | 4.5 | 4.7 |
| 60° C.- 14 days | Total amount of multimers (%) | 11.2 | 10.5 | 10.0 | 11.7 |

These results showed that the total amount of multimers and the formation of other multimers in hPM-1 antibody formulations can be remarkably inhibited by adding nonreducing disaccharides (sucrose, trehalose).

TABLE 15

| | | Sample 51 | Sample 52 | Sample 53 | Sample 54 |
|---|---|---|---|---|---|
| Anti-HM1.24 antibody (mg/mL) | | 10 | 10 | 10 | 10 |
| Polysorbate 80 (mg/mL) | | 0.25 | 0.25 | 0.25 | 0.25 |
| Acetate (mM) | | 30 | 30 | 30 | 30 |
| pH | | 6.0 | 6.0 | 6.0 | 6.0 |
| Additive (mM) | | — | Sucrose 145 | Trehalose 145 | Raffinose 145 |
| Initial | Dimers (%) | 2.8 | 2.8 | 2.8 | 2.8 |
| | Other multimers (%) | 0.5 | 0.5 | 0.5 | 0.5 |
| | Total amount of multimers (%) | 3.3 | 3.3 | 3.3 | 3.3 |
| Heat stress test | Dimers (%) | 9.2 | 10.4 | 9.5 | 9.9 |
| | Other multimers (%) | 5.6 | 2.9 | 4.1 | 4.3 |
| 60° C.- 14 days | Total amount of multimers (%) | 14.8 | 13.3 | 13.6 | 14.2 |

It was shown that the total amount of multimers and the formation of other multimers are remarkably inhibited by adding nonreducing disaccharides (sucrose, trehalose) in anti-HM1.24 antibody formulations similarly to hPM-1 antibody formulations.

Example 11

Effects of Adding Sugars (Light Acceleration Test)

The influence of adding sugars (nonreducing disaccharides and nonreducing trisaccharides) on stability during light acceleration was tested. Samples containing sugars shown in Tables 16 and 17 were prepared and subjected to a light acceleration test under the following conditions.

Stability during light acceleration was evaluated from the formation of dimers and multimers as determined by gel permeation chromatography (GPC).

TABLE 16

<Test samples and results>

| | | Sample 55 | Sample 56 | Sample 57 | Sample 58 |
|---|---|---|---|---|---|
| hPM-1 (mg/mL) | | 20 | 20 | 20 | 20 |
| Polysorbate 80 (mg/mL) | | 0.5 | 0.5 | 0.5 | 0.5 |
| Sodium Phosphate (mM) | | 15 | 15 | 15 | 15 |
| pH | | 6.5 | 6.5 | 6.5 | 6.5 |
| Additive (mM) | | — | Sucrose 145 | Trehalose 145 | Raffinose 145 |
| Initial | Dimers (%) | 0.4 | 0.4 | 0.4 | 0.4 |
| | Other multimers (%) | N.D. | N.D. | N.D. | N.D. |
| | Total amount of multimers (%) | 0.4 | 0.4 | 0.4 | 0.4 |
| Light acceleration test | Dimers (%) | 3.5 | 2.5 | 3.2 | 3.5 |
| | Other multimers (%) | N.D. | N.D. | N.D. | N.D. |
| 1,200,000 Lux · hr | Total amount of multimers (%) | 3.5 | 2.5 | 3.2 | 3.5 |

It was shown that the light-induced dimerization of hPM-1 antibody can be remarkably inhibited by adding sucrose.

TABLE 17

| | | Sample 59 | Sample 60 | Sample 61 | Sample 62 |
|---|---|---|---|---|---|
| Anti-HM1.24 antibody (mg/mL) | | 10 | 10 | 10 | 10 |
| Polysorbate 80 (mg/mL) | | 0.25 | 0.25 | 0.25 | 0.25 |
| Acetate (mM) | | 30 | 30 | 30 | 30 |
| pH | | 6.0 | 6.0 | 6.0 | 6.0 |
| Additive (mM) | | — | Sucrose 145 | Trehalose 145 | Raffinose 145 |
| Initial | Dimers (%) | 2.8 | 2.8 | 2.8 | 2.8 |
| | Other multimers (%) | 0.5 | 0.5 | 0.5 | 0.5 |
| | Total amount of multimers (%) | 3.3 | 3.3 | 3.3 | 3.3 |
| Light acceleration test | Dimers (%) | 3.8 | 4.1 | 3.4 | 3.1 |
| | Other multimers (%) | 2.8 | 0.8 | 2.8 | 2.9 |
| 1,200,000 Lux.hr | Total amount of multimers (%) | 6.6 | 4.9 | 6.2 | 6.0 |

It was shown that the light-induced association of anti-HM1.24 antibody can be remarkably inhibited by adding sucrose.

Example 12

Effects of Adding Surfactant Species

The influence of surfactant species on freeze/thaw stability was tested. Samples containing surfactants shown in Table 18 were prepared and tested as follows.

Stability to freeze/thaw cycling (3 cycles of freeze at −25° C./thaw at 4° C.) was evaluated from the number of particles per mL as measured by an automatic light obscuration particle counter (HIAC).

TABLE 18

<Test samples and results>

| | | Sample 63 | Sample 64 | Sample 65 | Sample 66 | Sample 67 | Sample 68 | Sample 69 | Sample 70 | Sample 71 | Sample 72 | Sample 73 | Sample 74 |
|---|---|---|---|---|---|---|---|---|---|---|---|---|---|
| HPM-1 (mg/mL) | | 4 | 4 | 4 | 4 | 4 | 4 | 4 | 4 | 4 | 4 | 4 | 4 |
| NaCl (mM) | | 250 | 250 | 250 | 250 | 250 | 250 | 250 | 250 | 250 | 250 | 250 | 250 |
| Sodium Phosphate (mM) | | 20 | 20 | 20 | 20 | 20 | 20 | 20 | 20 | 20 | 20 | 20 | 20 |
| pH | | 7.0 | 7.0 | 7.0 | 7.0 | 7.0 | 7.0 | 7.0 | 7.0 | 7.0 | 7.0 | 7.0 | 7.0 |
| Polysorbate 80 (mg/mL) | | 0 | 0.005 | 0.01 | 0.05 | 0.1 | 0 | 0 | 0 | 0 | 0 | 0 | 0 |
| Polysorbate 20 (mg/mL) | | 0 | 0 | 0 | 0 | 0 | 0.01 | 0.05 | 0.1 | 0 | 0 | 0 | 0 |
| Poloxamer 188 (mg/mL) | | 0 | 0 | 0 | 0 | 0 | 0 | 0 | 0 | 0.1 | 0.5 | 1 | 2 |
| Freeze/thaw (−25° C.→4° C., 3 cycles) | Number of particles of 10 μm or more (particles/mL) | 290 | 49 | 22 | 9 | 9 | 14 | 15 | 8 | 7 | 6 | 4 | 5 |
| | Number of particles of 25 μm or more (particles/mL) | 13 | 0 | 1 | 1 | 0 | 2 | 3 | 3 | 2 | 2 | 0 | 2 |

It was found that the formation of insoluble particles during freeze/thaw cycles is remarkably inhibited by the addition of surfactant species (Polysorbate 80, Polysorbate 20, Poloxamer 188).

The invention claimed is:

1. A stable solution pharmaceutical formulation comprising a humanized anti-interleukin-6 receptor IgG1 antibody in an amount from 17.5 to 22.5 mg/ml, sucrose in an amount from 25 to 100 mg/ml, surfactant as a stabilizer, and phosphate buffer, wherein the pH of the formulation is from 6.5 to 7.0, wherein the sucrose inhibits dimerization of the antibody.

2. The formulation according to claim 1, wherein the humanized anti-interleukin-6 receptor antibody comprises humanized PM-1 (hPM-1).

3. The formulation according to claim 1, wherein the antibody amount is 20 mg/ml.

4. The formulation according to claim 1, wherein the formulation is freeze-thaw stable.

5. The formulation according to claim 1, wherein the pH of the formulation is 6.5.

6. A freeze/thaw stable solution pharmaceutical formulation comprising humanized anti-interleukin-6 receptor IgG1 antibody in an amount from 17.5 to 22.5 mg/ml, sucrose in an amount from 25 to 100 mg/ml, surfactant as a stabilizers, and sodium phosphate buffer, wherein the pH of the formulation is about 6.5, wherein the sucrose inhibits dimerization of the antibody.

7. The formulation according to claim 6, wherein the humanized anti-interleukin-6 receptor antibody comprises humanized PM-1 (hPM-1).

8. The solution formulation according to claim 6, wherein the antibody amount is 20 mg/ml.

9. A stable solution pharmaceutical formulation comprising humanized anti-interleukin-6 receptor IgG1 antibody in an amount of from 17.5 to 22.5 mg/ml, 50 mg/ml sucrose, polysorbate 80 in an amount from 0.005 to 2 mg/ml, and phosphate buffer, wherein the pH of the formulation is about 6.5.

10. The formulation according to claim 9, wherein the humanized anti-interleukin-6 receptor antibody comprises humanized PM-1 (hPM-1).

11. The formulation according to claim 10, comprising 20 mg/ml hPM-1, 50 mg/ml sucrose, 0.5 mg/ml polysorbate 80, and 15 mM sodium phosphate, wherein the pH of the formulation is 6.5.

12. A freeze-thaw stable solution pharmaceutical formulation comprising 20 mg/ml humanized anti-interleukin-6 receptor IgG1 antibody PM-1 (hPM-1), 50 mg/ml sucrose, 0.5 mg/ml polysorbate 80, and 15 mM sodium phosphate buffer, wherein the pH of the formulation is 6.5.

13. The formulation according to claim 1, wherein the phosphate buffer is a sodium phosphate buffer.

14. The formulation according to claim 3, which is freeze-thaw stable.

15. The formulation according to claim 1, wherein the buffer concentration is from 10 to 20 mM.

16. The formulation according to claim 13, wherein the buffer concentration is from 10 to 20 mM.

17. The formulation according to claim 1, wherein the amount of surfactant in the formulation is from 0.005 to 2 mg/ml.

18. The formulation according to claim 1, in which the surfactant is a polyoxyethylene sorbitan fatty acid ester.

19. The formulation according to claim 1, wherein the surfactant is polysorbate 80.

20. The formulation according to claim 17, wherein the amount of polysorbate 80 in the solution is from 0.005 to 2 mg/ml.

21. The formulation according to claim 9, which is a freeze-thaw stable formulation, wherein the phosphate buffer is a sodium phosphate buffer.

* * * * *